United States Patent
Tsao et al.

(10) Patent No.: US 8,026,055 B2
(45) Date of Patent: Sep. 27, 2011

(54) MATERIALS AND METHODS FOR PROGNOSING LUNG CANCER SURVIVAL

(75) Inventors: Ming Sound Tsao, Tornoto (CA); Suzanne Lau, Willowdale (CA); Paul Boutros, North York (CA); Melania Pintilie, Thornhill (CA); Sandy Der, Toronto (CA); Frances A. Shepherd, Toronto (CA); Igor Jurisica, Toronto (CA); Linda Penn, Toronto (CA)

(73) Assignee: University Health Network, Toronto, Ontario (CA)

( * ) Notice: Subject to any disclaimer, the term of this patent is extended or adjusted under 35 U.S.C. 154(b) by 611 days.

(21) Appl. No.: 11/940,707

(22) Filed: Nov. 15, 2007

(65) Prior Publication Data

US 2008/0176236 A1  Jul. 24, 2008

Related U.S. Application Data

(60) Provisional application No. 60/865,960, filed on Nov. 15, 2006.

(51) Int. Cl.
*C12Q 1/00* (2006.01)

(52) U.S. Cl. ............................................... 435/6

(58) Field of Classification Search ................. None
See application file for complete search history.

(56) References Cited

U.S. PATENT DOCUMENTS

2004/0063120 A1  4/2004  Beer et al.

OTHER PUBLICATIONS

Tockman et al (Cancer Res., 1992, 52:2711s-2718s).*
Lau et al (Lung Cancer, 2005, 49(2): S283).*
Tockman et al (Cancer Res., 1992, 52:2711s-2718s).*
Lau, S, et al. Quantitative PCR validation of putative non-small cell lung cancer (NSCLC) prognostic marker genes derived from multiple published microarray databases and reports. Lung Cancer. Jul. 2005, vol. 49, Suppl. 2, p. S283.
Parmigiani, G., et al. A Cross-Study Comparison of Gene Expression Studies for the Molecular Classification of Lung Cancer. Clinical Cancer Research, May 2004, vol. 10, p. 2922-2927.

* cited by examiner

*Primary Examiner* — Sean Aeder
(74) *Attorney, Agent, or Firm* — Bereksin & Parr LLP; Micheline Gravelle; Carmela DeLuca

(57) ABSTRACT

The invention provides methods of prognosing and classifying lung cancer patients into poor survival groups or good survival groups. The invention also includes kits for use in the methods of the invention.

13 Claims, 7 Drawing Sheets

HARVARD

MICHIGAN

DUKE

HARVARD

MICHIGAN

MATERIALS AND METHODS FOR PROGNOSING LUNG CANCER SURVIVAL

This application claims the benefit under 35 USC §119(e) from U.S. Provisional patent application Ser. No. 60/865,960 filed Nov. 15, 2006, which is incorporated herein by reference in its entirety.

FIELD OF THE INVENTION

The invention relates to materials and methods for prognosing and classifying lung cancer, particularly non-small cell lung carcinomas (NSCLC).

BACKGROUND OF THE INVENTION

Non-small cell lung carcinomas (NSCLC) represent approximately 80% of lung cancers, with a dismal 5-year survival rate of 15%.[1] Tumor stage remains the strongest predictor of survival for these patients.[2] Early-stage (I to II) patients are treated primarily by complete surgical resection. However, 30-55% of these patients develop recurrence and die of the disease,[2, 3] implying that biological heterogeneity exists in patients and their tumors. Recent Phase 3 trials have established that adjuvant chemotherapy can significantly improve the survival of at least stage II-IIIA patients.[4-8] Therefore, identification of additional markers that may accurately classify early stage NSCLC patients into significantly different prognostic groups would improve the selection algorithm for patients to receive adjuvant therapy. To date, neither tumor histological features nor the >50 potential cancer-associated proteins that have been investigated could serve as such a marker.[9, 10]

Several NSCLC mRNA expression microarray studies have identified gene signatures that could subgroup patients into meaningful prognostic groups.[11-16] However, these putative prognostic gene lists are characterized more by discordance than concordance (FIG. 1A). Cross-study analyses of the datasets using different statistical approaches or validation using quantitative reverse transcriptase polymerase chain reaction (RT-qPCR) assays in an independent patient cohort have generated additional and different lists.[17-19] Such discordances may be attributed to insufficiently-powered studies,[20] and to variability in patient cohorts, expression profiling platforms or statistical methodologies. Further efforts to validate the prognostic value of these putative markers in large independent tumour/patient cohorts have been lacking.

There is a need to identify candidate markers to classify NSCLC patents into meaningful prognostic groups.

SUMMARY OF THE INVENTION

The inventors have identified a number of biomarkers which are differentially expressed in individuals with non-small cell lung carcinoma (NSCLC) according to different survival outcomes. The expression of these biomarkers can be used to prognose or classify patients with NSCLC into a poor survival group or a good survival group.

The invention provides methods of prognosing or classifying a subject with NSCLC into a poor survival group or a good survival group using the expression products of a minimal number of biomarkers. The expression products can include RNA products and protein products of the biomarkers. The inventors have identified 24 biomarkers as shown in Table 1 that can be used to prognose or classify a subject with NSCLC. In a specific embodiment, the inventors have identified a set of 3 (STX1A, CCR7 and HIF1A) and 6 (STX1A, HIF1A, CCT3, HLA-DPB1, MAFK and RNF5) classifiers or biomarkers that can be used in the methods of the invention.

Accordingly, one aspect of the invention is a method of prognosing or classifying a subject with non-small cell lung cancer, comprising the steps:
(a) determining the expression of a biomarker in a test sample from the subject, wherein the biomarker comprises one or more biomarkers as shown in Table 1;
(b) comparing the expression of the biomarker with a control,
wherein a difference in the expression of the biomarker between the control and the test sample is used to prognose or classify the subject with non-small cell lung cancer into a poor survival group or a good survival group.

Accordingly, one embodiment of the invention is a method of prognosing or classifying a subject with non-small cell lung cancer, comprising the steps:
(a) determining the expression of biomarkers in a test sample from the subject, wherein the biomarkers comprise STX1A, CCR7 and HIF1A;
(b) comparing the expression of the biomarkers with a control,
wherein a difference in the expression of the biomarkers between the control and the test sample is used to prognose or classify the subject with non-small cell lung cancer into a poor survival group or a good survival group.

A further embodiment of the invention is a method of prognosing or classifying a subject with non-small cell lung cancer, comprising the steps:
(a) determining the expression of biomarkers in a test sample from the subject, wherein the biomarkers comprise STX1A, HIF1A, CCT3, HLA-DPB1, MAFK and RNF5;
(b) comparing the expression of the biomarkers with a control,
wherein a difference in the expression of the biomarkers between the control and the test sample is used to prognose or classify the subject with non-small cell lung cancer into a poor survival group or a good survival group.

The prognoses and classifying methods of the invention can be used to select treatment. For example, the methods can be used to select or identify stage I and II patients who might (or might not) benefit from adjuvant chemotherapy. Specifically, stage I patients are typically not offered adjuvant chemotherapy since these patients have overall high survival rate of greater than 75% as a group. The minority portion of this group would potentially benefit from adjuvant chemotherapy but without means to identify these individuals, it is not reasonable to offer adjuvant therapy to the entire group. Therefore, the prognostic markers from this invention provide an opportunity to identify this subset of patients. In addition, anecdotal evidence indicates that although all Stage II patients are offered adjuvant chemotherapy, as much as one-third of them or more refuse this option for personal reasons such as a preference to avoid the side effects of chemotherapy. Furthermore, within a heterogeneous stage II group of patients, it is likely that some patients with excellent prognosis, despite being stage II, may not benefit significantly from adjuvant chemotherapy. Accurate prognostic markers to help identify those patients with truly poor survival would allow a physician to provide personalized advice and a stronger basis with which to suggest adjuvant therapies where necessary. Alternately, identification of patients with good prognosis using these markers would provide them with more information with which to make an informed decision regarding the choice of refusing adjuvant chemotherapy in order to be spared the side effects.

The invention also provides for kits used to prognose or classify a subject with NSCLC into a good survival group or a poor survival group that includes detection agents that can detect the expression products of the biomarkers.

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Figure 1A:
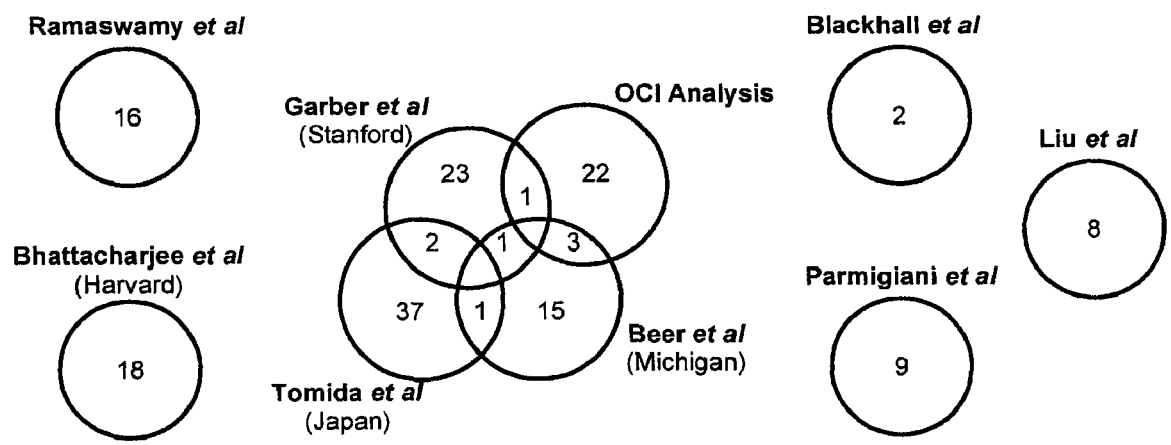
FIG. 1A is a Venn diagram that illustrates the lack of concordance among the 158 predictive genes identified in multiple microarray studies from groups at the Dana Farber Cancer Institute (Harvard),[11] Stanford,[12] Michigan,[13] Toronto[22] and Japan[16].

The invention relates to biomarkers which are differentially expressed in individuals with non-small cell lung carcinoma (NSCLC) according to different survival outcomes. These biomarkers can be used to prognose or classify individuals with NSCLC into a poor survival group or a good survival group.

The term "biomarker" as used herein refers to a gene that is differentially expressed in individuals with NSCLC and is predictive of different survival outcomes. The term "biomarker" includes one or more of the genes listed in Table 1.

Accordingly, one aspect of the invention is a method of prognosing or classifying a subject with non-small cell lung cancer, comprising the steps:

(a) determining the expression of a biomarker in a test sample from the subject, wherein the biomarker comprises one or more of the biomarkers as shown in Table 1;
(b) comparing the expression of the biomarker with a control, wherein a difference in the expression of the biomarker between the control and the test sample is used to prognose or classify the subject with non-small cell lung cancer into a poor survival group or a good survival group.

In one embodiment, the biomarkers comprise at least 2 biomarkers shown in Table 1.

In a specific embodiment, the biomarkers comprise the following minimal sets of genes or classifiers:

(i) STX1A, CCR7 and HIF1A; and/or
(ii) STX1A, HIF1A, CCT3, HLA-DPB1, MAFK and RNF5.

As used herein, the term "control" refers to a specific value that one can use to prognose or classify the value obtained from the test sample. In one embodiment, a dataset may be obtained from samples from a group of subjects known to have NSCLC and good survival outcome or known to have NSCLC and have poor survival outcome. The expression data of the biomarkers in the dataset can be used to create a control value that is used in testing samples from new patients. In such an embodiment, the "control" is a predetermined value for each biomarker or set of biomarkers obtained from NSCLC patients whose biomarker expression values and survival times are known. Using values from known samples allows one to develop an algorithm for classifying new patient samples into good and poor prognostic groups as described in the Example.

In another embodiment, the control can be an actual sample from a subject known to have NSCLC and good survival outcome or known to have NSCLC and have poor survival outcome.

A person skilled in the art will appreciate that the comparison between the expression of the biomarkers in the test sample and the expression of the biomarkers in the control will depend on the control used. For example, if the control is from a subject known to have NSCLC and poor survival, and there is a difference in expression of the biomarkers between the control and test sample, then the subject can be prognosed or classified in a good survival group. If the control is from a subject known to have NSCLC and good survival, and there is a difference in expression of the biomarkers between the control and test sample, then the subject can be prognosed or classified in a poor survival group. For example, if the control is from a subject known to have NSCLC and good survival, and there is a similarity in expression of the biomarkers between the control and test sample, then the subject can be prognosed or classified in a good survival group. For example, if the control is from a subject known to have NSCLC and poor survival, and there is a similarity in expression of the biomarkers between the control and test sample, then the subject can be prognosed or classified in a poor survival group.

The term "differentially expressed" or "differential expression" as used herein refers to a difference in the level of expression of the biomarkers that can be assayed by measuring the level of expression of the products of the biomarkers, such as the difference in level of messenger RNA transcript expressed or proteins expressed of the biomarkers. In a preferred embodiment, the difference is statistically significant. The term "difference in the level of expression" refers to an increase or decrease in the measurable expression level of a given biomarker as measured by the amount of RNA and/or the amount of protein in a sample as compared with the measurable expression level of a given biomarker in a control. In one embodiment, the differential expression can be compared using the ratio of the level of expression of a given biomarker or biomarkers as compared with the expression level of the given biomarker or biomarkers of a control, wherein the ratio is not equal to 1.0. For example, an RNA or protein is differentially expressed if the ratio of the level of expression in a first sample as compared with a second sample is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, a biomarker is identified as being differentially expressed as between a first sample and a second sample when the p-value is less than 0.1, preferably less than 0.05, more preferably less than 0.01, even more preferably less than 0.005, the most preferably less than 0.001.

The term "similarity in expression" as used herein means that there is no difference in the level of expression of the biomarkers between the test sample and the control. In a preferred embodiment, there is no statistically significant difference in the level of expression of the biomarkers.

The phrase "prognosing or classifying" as used herein refers to a method or process of determining whether an individual with NSCLC has a good or poor survival outcome, or grouping an individual with NSCLC into a good survival group or a poor survival group.

The term "good survival" as used herein refers to an increased chance of survival as compared to patients in the "poor survival" group. For example, the biomarkers of the invention can prognose or classify stage I patients into a "good survival group". These patients are at less risk of death 3 years after surgery.

The term "poor survival" as used herein refers to an increased risk of death as compared to patients in the "good survival" group. For example, biomarkers of the invention can prognose or classify stage I patients into a "poor survival group". These patients are at greater risk of death within 3 years from surgery.

The term "subject" as used herein refers to any member of the animal kingdom, preferably a human being that has NSCLC. In one embodiment the subject has early stage NSCLC. In a further embodiment, the subject has stage I NSCLC. In another embodiment, the subject has stage II NSCLC.

NSCLC patients are classified into stages, which are used to determine therapy. Staging classification include history, physical examination, routine laboratory evaluations, chest x-rays, and chest computed tomography scans with infusion of contrast materials. For example, stage I includes cancer in the lung, but has not spread to adjacent lymph nodes or outside the chest. Stage I is divided into two categories based on the size of the tumor (IA and IB). Stage II includes cancer located in the lung and proximal lymph nodes. Stage II is divided into 2 categories based on the size of tumor and nodal status (IIA and IIB). Stage III includes cancer located in the lung and the lymph nodes. Stage III is divided into 2 categories based on the size of tumor and nodal status (IIIA and IIIB). Stage IV includes cancer that has metastasized to distant locations. The term "early stage NSCLC" includes patients with Stage I to IIIA NSCLC. These patients are treated primarily by complete surgical resection.

The term "test sample" as used herein refers to any fluid, cell or tissue sample from a subject which can be assayed for biomarker expression products, particularly genes differentially expressed in subjects with NSCLC according to differential survival outcome. In one embodiment, the test sample is a cell, cells or tissue from a tumor biopsy from the subject.

The phrase "determining the expression of biomarkers" as used herein refers to determining or quantifying RNA or proteins expressed by the biomarkers. The term "RNA" includes mRNA transcripts, and/or specific spliced variants of mRNA. The term "RNA product of the biomarker" as used herein refers to RNA transcripts transcribed from the biomarkers and/or specific spliced variants. In the case of "protein", it refers to proteins translated from the RNA transcripts transcribed from the biomarkers. The term "protein product of the biomarker" refers to proteins translated from RNA products of the biomarkers.

A person skilled in the art will appreciate that a number of methods can be used to detect or quantify the level of RNA products of the biomarkers within a sample, including microarrays, RT-PCR (including quantitative RT-PCR), nuclease protection assays and Northern blot analyses.

In addition, a person skilled in the art will appreciate that a number of methods can be used to determine the amount of a protein product of the biomarker of the invention, including immunoassays such as Western blots, ELISA, and immunoprecipitation followed by SDS-PAGE and immunocytochemistry.

Conventional techniques of molecular biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995).

The method of the invention can be used to select treatment for NSCLC patients. As explained herein, the biomarkers can classify patients with NSCLC into a poor survival group or a good survival group. In one embodiment, the patients have early stage NSCLC. In another embodiment, the patients have stage I NSCLC. Thus, the method of the invention can be used to classify patients with NSCLC, early stage NSCLC and/or stage I NSCLC into groups that might benefit from adjuvant chemotherapy or not.

The invention also provides for kits used to prognose or classify a subject with NSCLC into a good survival group or a poor survival group that includes detection agents that can detect the expression products of the biomarkers.

A person skilled in the art will appreciate that a number of detection agents can be used to determine the expression of the biomarkers. For example, to detect RNA products of the biomarkers, probes, primers, complementary nucleotide sequences or nucleotide sequences that hybridize to the RNA products can be used. To detect protein products of the biomarkers, ligands or antibodies that specifically bind to the protein products can be used.

The term "nucleic acid" includes DNA and RNA and can be either double stranded or single stranded.

The term "hybridize" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. may be employed.

The term "primer" as used herein refers to a nucleic acid sequence, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art. The term "primer" as used herein refers a set of primers which can produce a double stranded nucleic acid product complementary to a portion of the RNA products of the biomarker or sequences complementary thereof.

The term "probe" as used herein refers to a nucleic acid sequence that will hybridize to a nucleic acid target sequence. In one example, the probe hybridizes to an RNA product of the biomarker or a nucleic acid sequence complementary thereof. The length of probe depends on the hybridize conditions and the sequences of the probe and nucleic acid target sequence. In one embodiment, the probe is at least 8, 10, 15, 20, 25, 50, 75, 100, 150, 200, 250, 400, 500 or more nucleotides in length.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Antibodies having specificity for a specific protein, such as the protein product of a biomarker, may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the peptide and the monoclonal antibodies can be isolated.

A person skilled in the art will appreciate that the detection agents can be labeled.

The label is preferably capable of producing, either directly or indirectly, a detectable signal. For example, the label may be radio-opaque or a radioisotope, such as $^3H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

Accordingly, the invention includes a kit to prognose or classify a subject with non-small cell lung cancer, comprising detection agents that can detect the expression products of biomarkers, wherein the biomarkers comprise at least one biomarker as shown in Table 1. In a specific embodiment, the biomarkers comprise STX1A, CCR7 and HIF1A. In another specific embodiment, the biomarkers comprise STX1A, HIF1A, CCT3, HLA-DPB1, MAFK and RNF5.

The kit can also include a control or reference standard and/or instructions for use thereof. In addition, the kit can include ancillary agents such as vessels for storing or transporting the detection agents and/or buffers or stabilizers.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

EXAMPLES

Summary

Several microarray studies have reported gene expression signatures capable of classifying non-small cell carcinoma (NSCLC) patients according to different survival outcomes. However, the reported predictive gene lists do not overlap across studies, and have not been extensively validated independently and/or using other assay methods.

The expression of 158 putative prognostic genes identified in previous microarray studies was retrospectively studied by reverse transcription (RT)-quantitative polymerase chain reaction (qPCR) in snap-frozen banked tumors of 168 NSCLC patients. Two distinct statistical methods were employed to identify stable gene subsets that were robust classifiers of patient prognosis.

Overlapping six- and three-gene classifiers capable of separating the training cohort into two distinct patient groups with significantly different survival outcome were found (stage-independent hazard ratio for death, 5.5; P<0.001 and hazard ratio, 3.7; P<0.001, respectively). The prognostic power of each classifier was validated on three independent microarray datasets from the Dana Farber Cancer Institute (herein referred to as the Harvard dataset),[11] the University of Michigan (Michigan),[13] and Duke University (Duke).[21] Furthermore, the classifiers were able to substage stage I patients into significantly different prognosis.

In summary, the inventors have shown that resected NSCLC patients can be molecularly staged by minimal gene expression classifiers, which can be used to select patients for adjuvant chemotherapy.

Materials and Methods

Patients and Tissue Samples

This study was carried out using 168 snap-frozen banked tumor samples from patients who were primarily treated by lobectomy or pneumonectomy at the Toronto General Hospital (1996-00) and the Mount Sinai Hospital (1995-98). Tissues were harvested within 30 min after complete resection, and the quality and pathology of tumor tissue was confirmed by the study pathologist. The tissues were banked with informed consent, and the University Health Network Research Ethics Board approved this study protocol.

Assembly of Prognostic Gene Candidates

To assemble the 158 genes for RT-qPCR validation, 128 genes were derived from putative prognostic gene sets in published NSCLC microarray and validation studies,[11-13, 15-17, 22] and the inventors independently identified a unique list of 22 poor prognosis genes in patients with KRAS mutations from the Michigan dataset[13] using overlapping binary tree-structured vector quantization (BTSVQ) and Significance Analysis of Microarrays (SAM) analysis[23]. Eight additional genes were included from a previously published orthotopic rodent model of metastatic human NSCLC.[24]

Expression Analysis by RT-qPCR

Expression levels were determined using quantitative reverse transcriptase polymerase chain reaction (RT-qPCR) and are represented by absolute gene transcript copy numbers per nanogram of cDNA.[26] To control for variability in cDNA quantity, integrity and the overall transcriptional efficiency of individual primers, RT-qPCR data was subjected to standardization and normalization against a panel of four housekeeping genes as previously described[27]. Poor quality samples were also removed, leaving a final cohort of 147 patients.

Statistical Analysis

The endpoint for analysis was overall survival, which was defined as the time between surgery and the event (death). Data was considered censored when an event did not occur, and survival was calculated between surgery and the last follow-up date available. The goal of this study was to choose a set of genes highly predictive of outcome. The methods of modified Steepest Descent (mSD) and Risk Score (RS) assignation were used to identify gene classifiers whose mRNA expression profiles were predictive of patient prognosis. Survival differences between prognostic groups were then tested using the log-rank test, and multivariate analysis was performed by Cox proportional hazards models.

mSD combined a greedy, gradient descent feature selection algorithm and unsupervised machine-learning to identify a prognostic classifier.[28] All possible one-gene classifiers were first considered, using expression to separate patients into two groups through k-medians clustering. The survival differences between these two groups were assessed using log-rank analysis, and the single gene that performed best was included in the final classifier. Next, all two-gene sets containing the single best gene were considered, with patients again grouped and survival differences tested in the same manner as before. The best second gene was then kept in the final classifier, and the process iterated until a final n-gene classifier was found whose performance was not exceeded by any n+1 gene superset of itself.

The RS method employed a standard approach for identifying prognostic genes and risk score modeling with several key differences. First, the concordance index (C-Index) was used instead of p-values for thresholding. C-Index values quantify the level of concordance between observed and predicted values for a given model with values ranging from 0.5 (poor predictive ability) to 1.0 (excellent predictive ability).[29, 30] The C-Index of each individual gene was calculated; genes with a concordance $\geq 0.65$ were considered to have possible prognostic value. Second, in order that the contribution of each of these genes was accurately reflected in the coefficients of the Cox proportional hazards model, expression levels for these genes were further standardized by centering to the mean and scaling to the standard deviation. Third, a discretized risk score was then assigned to each gene based on its coefficient in the Cox model developed independently of clinical data. A composite score was calculated for each patient by adding the risk scores of genes whenever the gene had a positive value prior to standardization. Based on the distribution of the RS, the patient cohort was divided into two groups by median dichotomization (good vs. poor prognosis). To assess the impact of including gene expression data in the prognostic model, C-Index values were also calculated for models containing both clinical and expression data. Only 137 patients with complete clinical (stage and histology) and gene expression data were included in this analysis.

Independent Validation

Raw data from the previously published lung adenocarcinoma mRNA expression profiles were obtained.[11, 13, 21] To allow for direct comparisons between the different microarray platforms and RT-qPCR data, array data was subjected to normalization and median-scaling as described previously.[25]

For classification with the 6-gene mSD subset, patients from the microarray datasets were directed into one of two prognostic groups based on the distance separating their gene-expression profiles from the good and poor cluster centres, and were subjected to a quality criterion (see below). For the weighted RS model, patients were classified based on the criteria established developed on the UHN patient set. Since the Harvard and Michigan datasets contained only patients with adenocarcinomas, the clinical risk score model contained only stage information. C-Index values were calculated for the clinical model alone, as well as for models containing both clinical and expression data.

New Patient Classification: mSD

To classify new patients that were not present in the training set into one of the two groups for validation purposes, standard Euclidean distances were calculated between a new patient's expression-profile and the median expression-profile of each of the two clusters. A patient is then classified into the nearest of the two clusters. For example, consider a two-gene classifier where the two patient groupings have median expression values of (X1, X2) for the good prognosis group and (Y1, Y2) for the poor prognosis group. For a new patient with expression values (Z1, Z2), we would calculate the Euclidean distance to each cluster as:

$$\text{Distance to cluster 1} = \text{Dist1} = \text{Sqrt}[(X_1-Z_1)^2+(X_2-Z_2)^2]$$

$$\text{Distance to cluster 2} = \text{Dist2} = \text{Sqrt}[(Y_1-Z_1)^2+(Y_2-Z_2)^2]$$

If Dist1 is smaller than Dist2, we would then place the patient in cluster 1, or vice versa. It is possible, however, for cases to arise where a patient is nearly equidistant between the two clusters. That is, when Dist1 is approximately as large as Dist2. In such cases, a patient cannot be classified. This so-called "quality criterion" is developed from the training dataset, and is imposed on the ratio (Dist1/Dist2) to identify the patients that are nearly equidistant from the two clusters. In the context of the clinic, patients with these indeterminate expression profiles would receive the current standard of care. A quality criterion was selected by selecting the score that optimized leave-one-out cross-validation performance in the Toronto dataset, and this criterion was applied to all validation datasets.

New Patient Classification: Risk Score

A composite risk score, as defined in the Toronto cohort, was calculated for each validation patient using expression values prior to standardization. Patients were classified according to the median dichotomization threshold identified in the Toronto dataset.

Results

Univariate survival analysis of expression data from 147 UHN patients demonstrated enrichment for prognostic markers, with 24 of the 158 genes (15%) significant at p≦0.05 (Table 1). Seven remained significant after a false-discovery rate adjustment for multiple-testing (q≦0.05). Ontology over-representation analysis found an excess of prognostic genes were involved in the maintenance of cellular homeostasis.[44] To identify multiple prognostic classifiers, the mSD and RS algorithms were applied.

mSD Gene Classifier Prediction Method

Figure 1B:
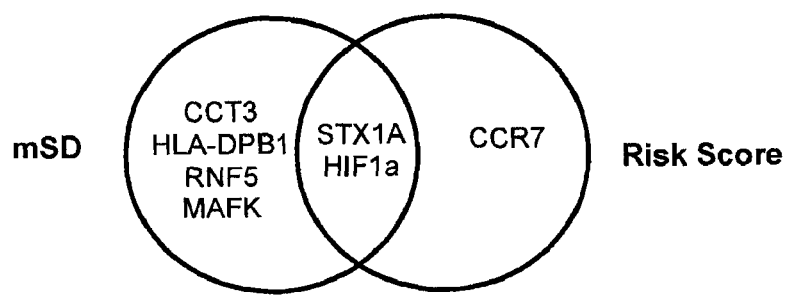
FIG. 1B is a Venn diagram showing the overlapping 6- and 3-gene classifiers identified using the mSD and RS selection methods.
Figure 1C:
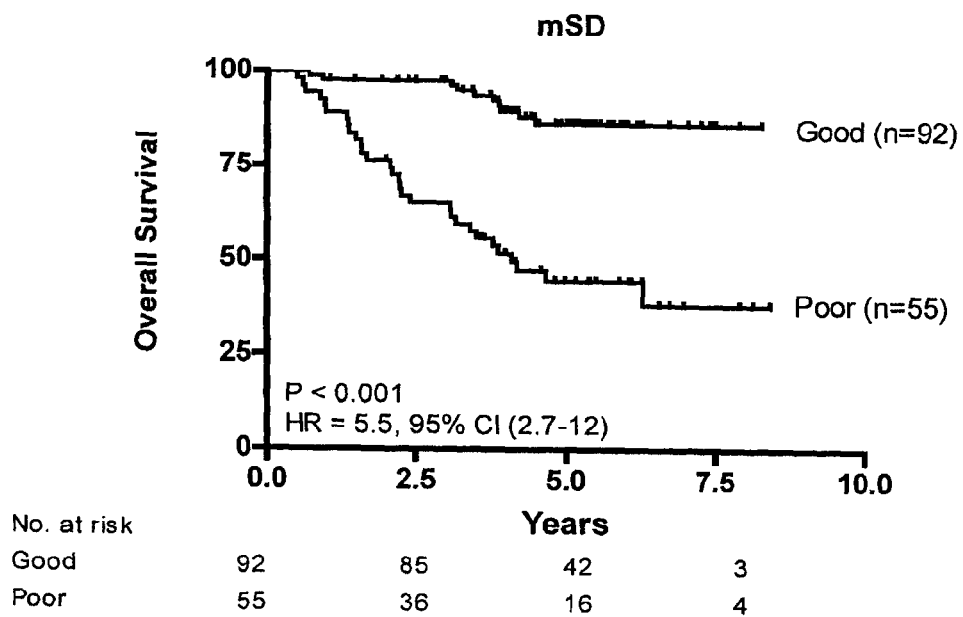
FIG. 1C shows the mSD 6-gene classifier and FIG. 1D shows the 3-gene RS model. The classifiers further improve upon current staging methods. Overall survival of Stage I patients is shown in FIG. 1E by the mSD classifier and in FIG. 1F by the RS classifier.

A 6-gene classifier (STX1A, HIF1A, CCT3, HLA-DPB1, MAFK and RNF5) (Table 2) capable of separating the 147 patients into two groups with significantly different overall survival (hazard ratio for death, 5.5; 95 percent confidence interval, 2.7-12; P<0.001) (Table 3, FIG. 1B) was identified.

RS Classifier Prediction Method

Figure 1D:
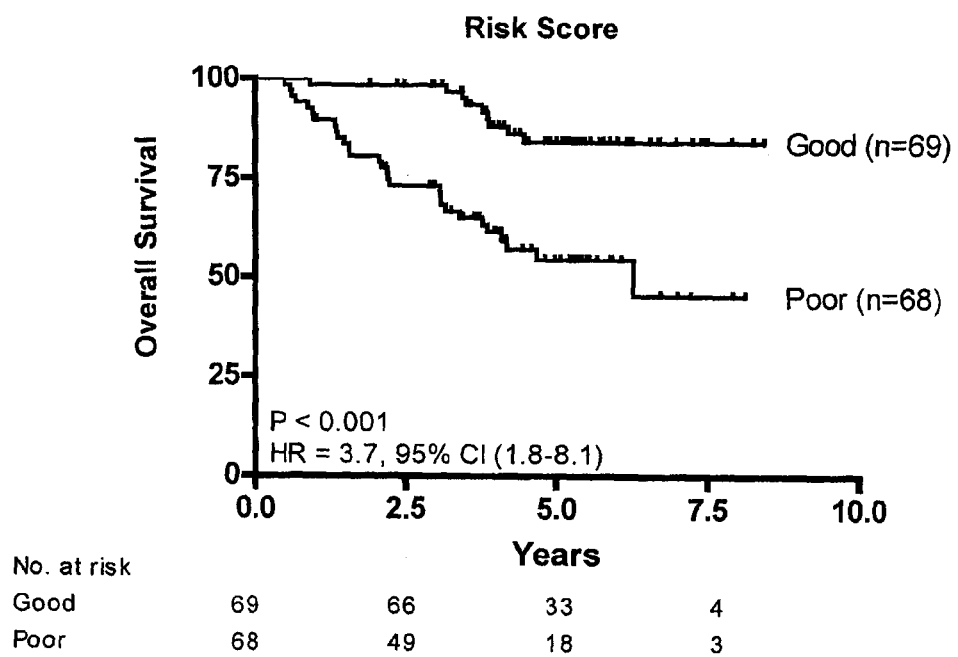

A 5-gene classifier (STX1A, CCR7, HIF1A, PAFAH1B3, and CCT3) using a C-Index threshold of ≧0.65 (Tables 2 and 4) was identified. However, neither PAFAH1B3 nor CCT3 were found to improve the classification ability of the RS model that consisted of the top 3 genes (STX1A, CCR7 and HIF1A); the latter was used for remaining analyses. In the weighted model, STX1A, CCR7 and HIF1A were assigned values of +4, −3 and +3, respectively (Table 4). Based a median dichotomization of the composite risk scores, patients scoring ≦2 were considered to have good prognosis, while patients scoring >2 were classified in the poor prognosis group. These genes were capable of separating patients into two groups with significantly different outcomes (hazard ratio, 3.7; 95 percent confidence interval, 1.8-8.2; p<0.001) (Table 3, FIG. 1D). Improvement in C-Index values was also observed when stage and histology were included in the model (Table 5).

Comparison Between mSD and RS

The classification of patients into good and poor prognosis groups using mSD and RS showed significant correlation (Table 6). The mSD algorithm is more likely not to classify a patient with intermediate expression patterns. This however, does not affect the separation efficiency of the algorithm (Table 3). RS can classify all patients with complete clinical annotation since it relies on median dichotomization of the cohort, and does not contain a quality criterion.

Substaging

Figure 1E:
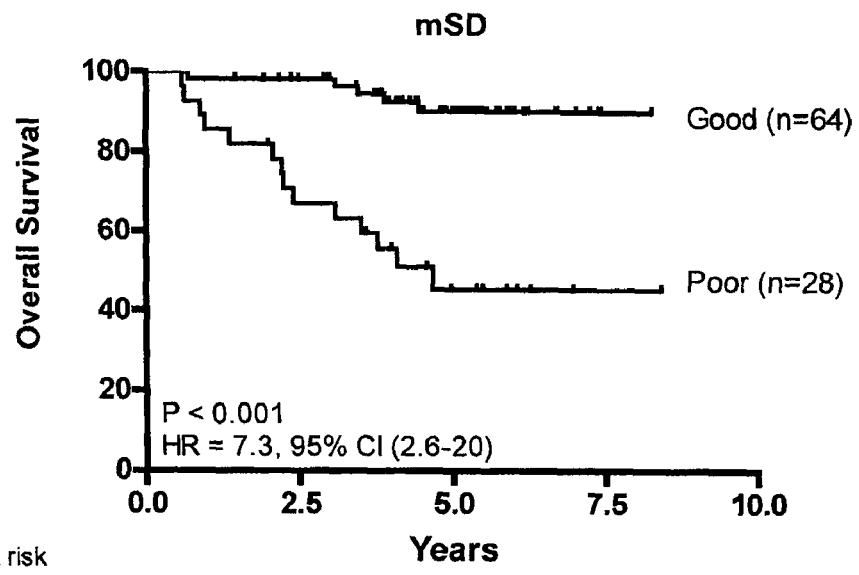
Figure 1F:
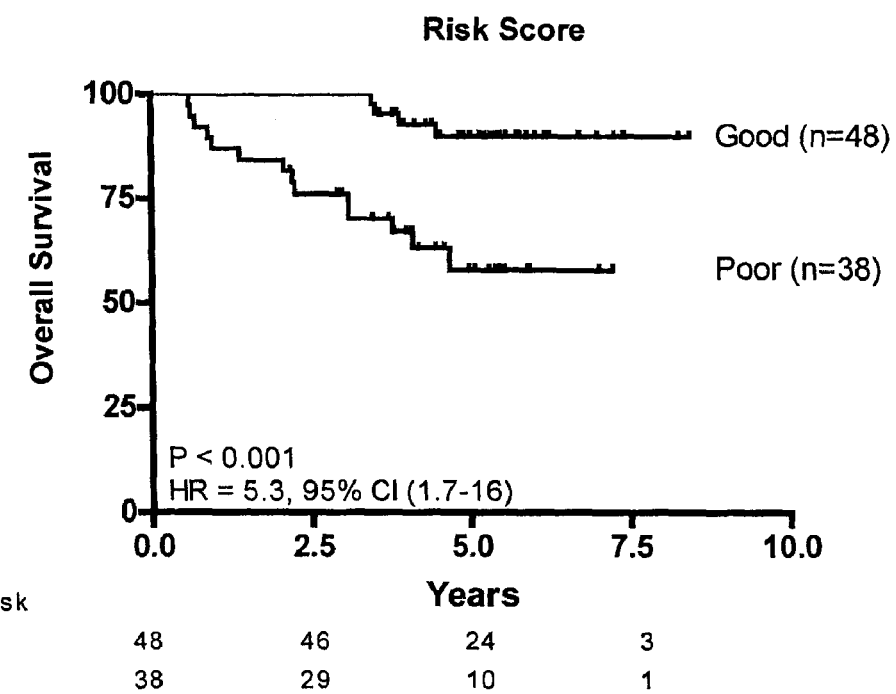

The classifiers were tested for their ability to substage stage I patients. Compared to pathological stage alone, both mSD and RS classifiers demonstrated significant improvement in classification ability (hazard ratios, 7.3 and 5.3; 95 percent confidence intervals, 2.6-20 and 1.7-16, respectively; both P<0.001) (FIGS. 1E-F). With both classifiers, at least 16.5 fold more (33% vs. 2% for mSD and 24% vs. 0% for RS) stage I patients classified as "poor prognosis" were at risk of death after 3 years than "good prognosis" patients (Table 7).

Independent Validation

Figure 2:
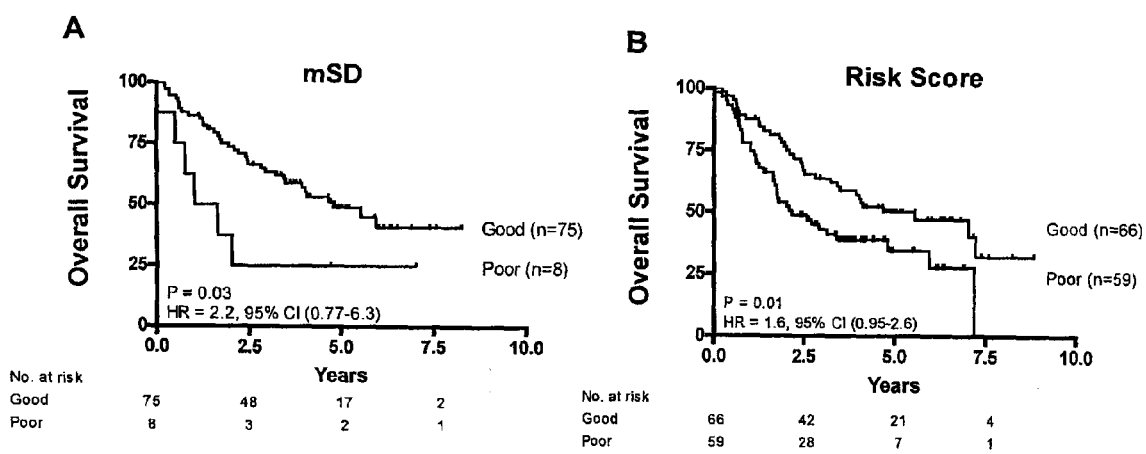
FIG. 2 is a validation of classifiers in three independent patient sets. Overall survival curves predicted for the mSD 6-gene classifier and the 3-gene RS model for the Harvard dataset (A-B), the Michigan dataset (C-D) and the Duke dataset (E-F).
Figure 2:
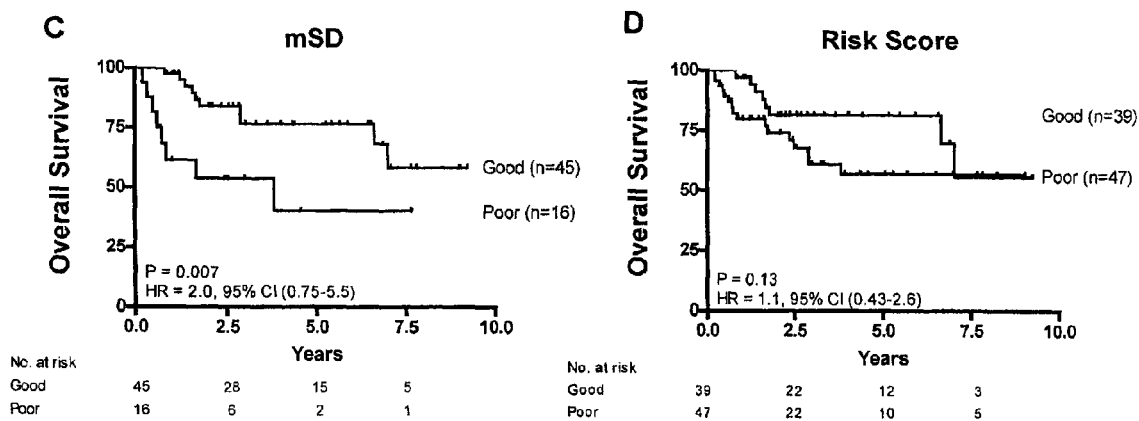
Figure 2:
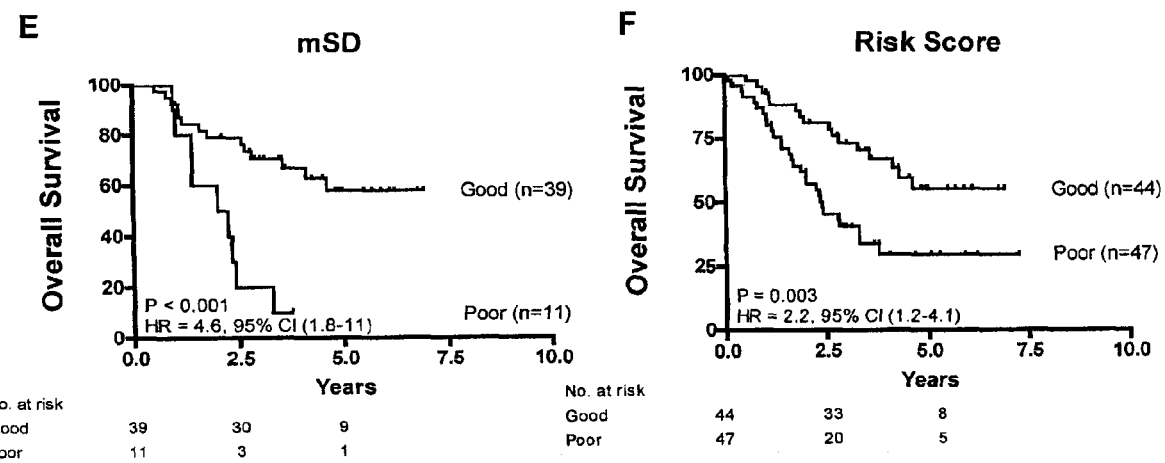
Figure 3:
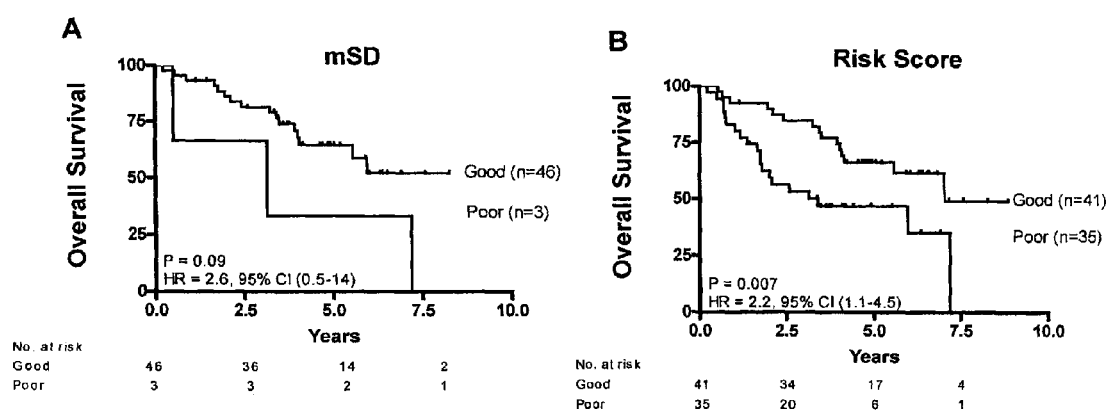
FIG. 3 shows overall survival curves predicted for Stage I patients by the mSD and RS classifiers for the Harvard dataset (A-B), Michigan dataset (C-D) and Duke dataset (E-F).
Figure 3:
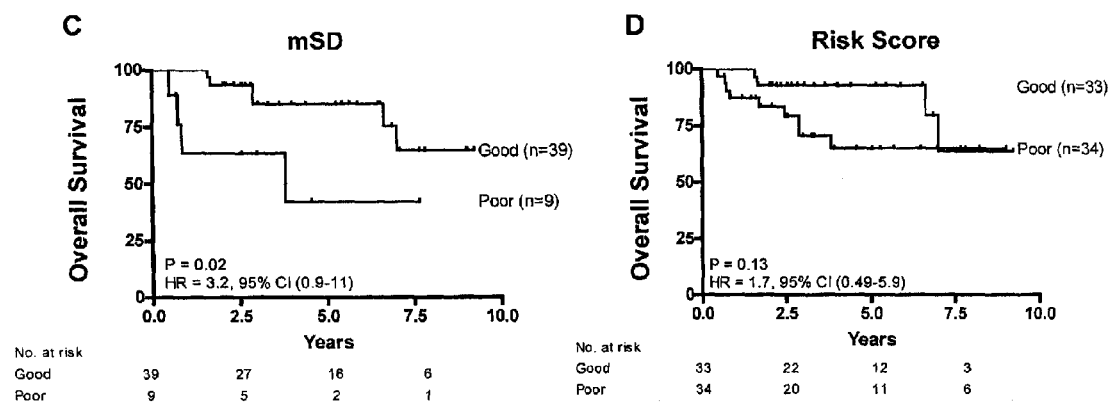
Figure 3:
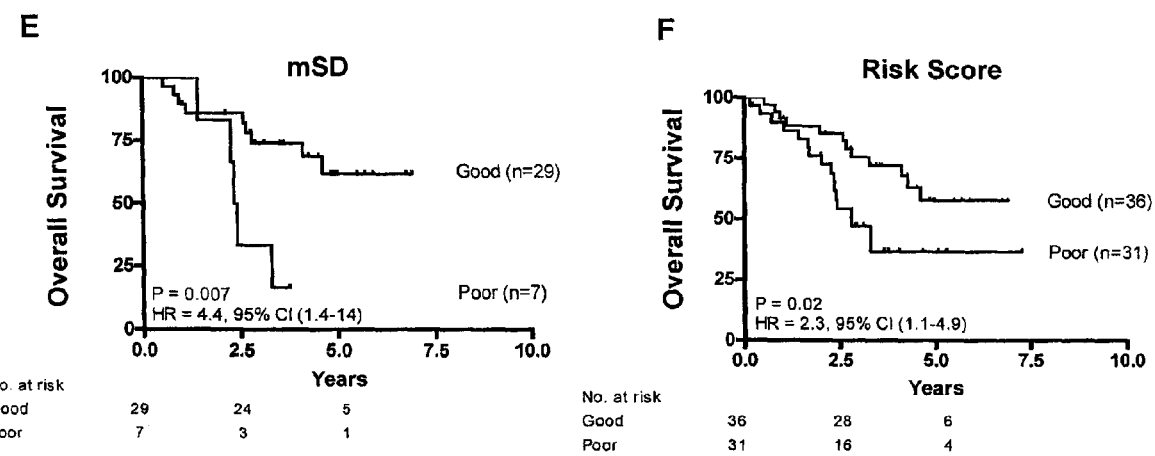

The robustness of the two classifiers was tested for survival prediction in three independent microarray datasets from Harvard, Michigan and Duke. In all cohorts, the prognostic significance of mSD classifier was validated (hazard ratios, 2.2, 2.0 and 4.6; 95 percent confidence intervals, 0.77-6.3, 0.75-5.5 and 1.8-11; p=0.030, 0.007 and <0.001, respectively) (Table 3, FIGS. 2A, 2C and 2E), although a proportion of cases in each were excluded as indeterminate by the quality criterion for the algorithm. The RS model was prognostic in the Harvard and Duke patients (hazard ratios, 1.9 and 2.2; 95 percent confidence intervals, 1.1-3.1 and 1.2-4.1, respectively; both p=0.003) (Table 3, FIGS. 2B and 2F). The separation was not significant in the Michigan cohort (hazard ratio, 1.1; 95 percent confidence interval, 0.49-5.9; p=0.13), which included only stage I and III adenocarcinoma patients (Table 3, FIG. 2D). It furthermore demonstrated improvement over the clinical model alone for the Duke patients (Table 5). Both classifiers also demonstrated significant or trend to significant ability to substage stage I patients into poor and good prognosis groups (Table 3, FIG. 3A-F), with a greater percentage of patients at risk of dying at 3 years (Table 7).

Discussion

Despite wide discordance among the signature gene sets identified in various lung cancer microarray studies, the inventors have demonstrated through the use of RT-qPCR in an independent patient cohort that these studies have enriched for genes with prognostic value in NSCLC. By using an assay that quantifies mRNA transcript number in tumor samples, minimal sets of 3- and 6-gene subsets can classify early-stage NSCLC patients into subgroups with significantly different prognosis, and the strength of these classifiers is robustly reproduced across 3 independent publicly available microarray databases.

Steepest descent is a well-characterized optimization procedure for identifying the minima of a dataset.[28] The key advantage of mSD is its computationally efficient, unbiased nature, with essentially no parameterization. Secondly, the quality-criterion gives a measure of confidence for each prediction made. A third advantage is the ability of mSD classifiers to use partial information by not considering missing dimensions during patient classification. For example, MAFK was not present on the Hu6800 chip of the Michigan study,[13] but mSD classification ignored this dimension, and successfully predicted prognosis from the remaining five dimensions. In theory, steepest-descent algorithms can suffer from overfitting, and the proportion of unclassified cases can be variable. Nevertheless, the results were not found to be sensitive to perturbations in the quality criterion, and the classifier validated in all datasets, suggesting that over-fitting did not occur.

Risk scores are a well-established method for the classification of patients into prognostic arms.[33,34] The modifications presented in the RS model enable the identification of gene classifiers that predict prognosis without the inclusion of clinical information in the model. The increase in C-Index scores, representing an improvement in predictive power, observed between a clinical model and one incorporating the expression data from the 3-gene classifier suggests that expression patterns are both independent of, and enhance the predictive ability of clinical parameters such as stage and histology.

The results have demonstrated that the predictive gene lists identified by both subset selection methods are reproducible, even when applied to microarray expression data. Although these studies used three generations of Affymetrix microarray chips (Hu6800, HG_U95Av2 and HG_U133 Plus 2.0) and considered cohorts with different clinical features, these effects appeared to be minimized upon appropriate normalization of the data.

Wigelt et al.[35] have suggested that not all genes in prognostic signatures have a role in tumorigenesis. Thus, it is no surprise that few of the genes identified by the subset selection methods have been extensively characterized in the context of NSCLC. Of the two genes found in common between the presented classification methods (FIG. 1B), only HIF1A has been studied in detail, but only at the protein level.[36] Yet, STX1A is deregulated in small cell lung cancer, and has been associated with more aggressive forms of colon and rectal carcinomas,[37,38] while Syntaxin 2, with more than 70% similarity to STX1A, has a transforming role in mouse mammary tissue.[39] Interestingly, the inventors found several of the classifier genes consistently differentially expressed by RT-qPCR in matched normal and tumor NSCLC samples, which were also verified in public microarray studies. These genes may therefore represent attractive targets for future biological and mechanistic studies.

Although the NSCLC classifier is effective independent of conventional clinicopathological prognosticators such as pathological stage and histology, the predictive power of this classifier is significantly enhanced when combined with these standard prognosticators. Importantly, this classifier is capable of identifying at least twice as many stage I patients at risk of disease recurrence/death in the "poor" versus the "good" prognosis group all stage I patients. This indicates that molecular classifiers are capable of substaging and selecting patients who may benefit from adjuvant chemotherapy. Exploratory subgroup analysis of the Phase 3 JBR.10 and ANITA trials revealed that stage IB patients did not benefit from adjuvant chemotherapy.6, 8 Although the stage IB-restricted CALGB 9633 trial initially reported significant survival benefit from adjuvant chemotherapy with paclitaxel and carboplatin, significant benefit in overall survival was no longer observed with prolonged follow-up despite maintaining its benefit in disease-free survival.7 If further validated in additional independent patient cohorts, the gene classifiers could potentially be tested prospectively with a biomarker-based assay in a clinical trial to identify stage I patients who might benefit from adjuvant chemotherapy.

Two studies have recently also identified prognostic markers for NSCLC.[40, 41] Potti et al.[40] used a metagene-derived model in combination with clinical data to substage stage IA NSCLC patients based on their risk of recurrence. Raponi et al.[41] described a squamous cell carcinoma specific gene signature that could predict prognosis.[13] These two models included dozens or hundreds of genes, as do many other putative prognostic marker panels,[42, 43] and will therefore rely on microarray platforms for analysis. In contrast, the potentially significant advantage of our minimal classifiers is that they may be implemented clinically using cost-effective multiplex assays. Although the number of microarray studies surveyed limited the scope of our validation, our results indicate that minimal gene classifiers can robustly predict prognosis in NSCLC patients.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

The 24 genes found to be significant in univariate analysis (p < 0.05).

| # | Gene Symbol | RefSeq ID | Unigene Cluster | SwissProt ID | P Values | HR* | HR Lower | HR Upper | Description |
|---|---|---|---|---|---|---|---|---|---|
| 1 | ACTR3 | NM_001655 | Hs.433512 | P61158 | 0.0243 | 1.5005 | 1.0551 | 2.1341 | ARP3 actin-related protein 3 homolog (yeast) |
| 2 | CALCA | NM_001741 | Hs.37058 | P01258 | 0.0007 | 1.0907 | 1.0348 | 1.1495 | calcitonin/calcitonin-related polypeptide, alpha |
| 3 | CCR7 | NM_001838 | Hs.370036 | P32248 | 0.0002 | 0.7706 | 0.6705 | 0.8856 | chemokine (C-C motif) receptor 7 |
| 4 | CCT3 | NM_005998 | Hs.491494 | P49368 | 0.0004 | 1.8514 | 1.3123 | 2.6122 | chaperonin containing TCP1, subunit 3 |
| 5 | CPE | NM_001873 | Hs.75360 | P16870 | 0.0028 | 1.3872 | 1.1188 | 1.7201 | carboxypeptidase E |
| 6 | EIF4E2 | NM_004846 | Hs.292026 | O60573 | 0.0113 | 1.7519 | 1.1316 | 2.7124 | eukaryotic translation initiation factor 4E member 2 |
| 7 | FADD | NM_003824 | Hs.86131 | Q13158 | 0.0044 | 1.5131 | 1.1450 | 1.9996 | Fas (TNFRSF6)-associated via death domain |
| 8 | GAPDH | NM_002046 | Hs.479728 Hs.544577 Hs.592355 Hs.598544 | P04406 | 0.0274 | 1.3014 | 1.0284 | 1.6469 | Glyceraldehyde-3-phosphate dehydrogenase |
| 9 | HIF1A | NM_001530 | Hs.509554 Hs.597216 | Q16665 | 0.0070 | 1.3668 | 1.1252 | 1.6603 | hypoxia-inducible factor 1, alpha subunit (basic helix-loop-helix transcription factor) |
| 10 | HLA-DPB1 | NM_002121 | Hs.485130 | O00259 | 0.0195 | 0.7502 | 0.5894 | 0.9548 | MHC Class II, DPbeta1 |
| 11 | IRX5 | NM_005853 | Hs.435730 | P78411 | 0.0254 | 0.8007 | 0.6616 | 0.9691 | iroquois homeobox protein 5 |
| 12 | LOC158381 | NM_001029857 | Hs.575661 | NA | 0.0287 | 1.2392 | 1.0226 | 1.5017 | hypothetical protein LOC158381 |
| 13 | MARCH6 | NM_005885 | Hs.432862 | O14670 | 0.0168 | 1.6207 | 1.0901 | 2.4094 | membrane-associated RING-CH protein VI |
| 14 | NAP1L1 | NM_004537 | Hs.524599 Hs.643135 | P55209 | 0.0297 | 1.3660 | 1.0349 | 1.7505 | nucleosome assembly protein 1-like 1 |
| 15 | NFYB | NM_006166 | Hs.84928 | P25208 | 0.0070 | 1.8415 | 1.1892 | 2.8515 | nuclear transcription factor Y, beta |
| 16 | PAFAH1B3 | NM_002573 | Hs.466831 | Q15102 | 0.0022 | 1.5393 | 1.1693 | 2.0263 | platelet-activating factor acetylhydrolase, isoform lb, gamma subunit 29kDa |
| 17 | PLGLB1 | NM_002665 | Hs.450026 | NA | 0.0418 | 1.3222 | 1.0119 | 1.7276 | plasminogen-like B1 |
| 18 | PLOD2 | NM_000935 | Hs.477866 | O00469 | 0.0320 | 1.2687 | 1.0227 | 1.5738 | procollagen-lysine, 2-oxoglutarate 5-dioxygenase (lysine hydroxylase) 2 |
| 19 | SELP | NM_003005 | Hs.73800 | P16109 | 0.0319 | 0.8616 | 0.7511 | 0.9884 | selectin P (granule membrane protein 140kDa, antigen CD62) |
| 20 | SPRR1B | NM_003125 | Hs.1076 | P22528 | 0.0050 | 1.8789 | 1.2082 | 2.9219 | small proline-rich protein 1B (cornifin) |
| 21 | STC1 | NM_003155 | Hs.25590 | P52823 | 0.0108 | 1.2898 | 1.0638 | 1.5639 | stanniocalcin 1 |
| 22 | STX1A | NM_004603 | Hs.520943 | Q16623 | 0.0000 | 1.6342 | 1.2989 | 2.0560 | syntaxin 1A (brain) |
| 23 | THRAP2 | NM_015335 | Hs.159799 | Q71F56 | 0.0146 | 1.6957 | 1.1166 | 2.5752 | thyroid hormone receptor associated protein 2 |

TABLE 1-continued

The 24 genes found to be significant in univariate analysis (p < 0.05).

| Gene # | Gene Symbol | RefSeq ID | Unigene Cluster | SwissProt ID | P Values | HR* | HR Lower | HR Upper | Description |
|---|---|---|---|---|---|---|---|---|---|
| 24 | XRCC6 | NM_001469 | Hs.292493 | P12956 | 0.0033 | 1.6654 | 1.1824 | 2.3457 | X-ray repair complementing defective repair in Chinese hamster cells 6 (Ku autoantigen, 70kDa) |

*An HR value of greater than 1 suggests that individuals with higher expression of that gene are more likely to have poor prognosis. An HR value of less than 1 suggests that individuals with higher expression of that gene are more likely to have good prognosis.

TABLE 2

Genes identified as having prognostic value by the mSD and RS methods.

| Method | Gene Symbol | Entrez Gene ID | Gene annotation | HR* | 95% CI | P |
|---|---|---|---|---|---|---|
| Both Classifiers | STX1A | 6804 | syntaxin 1A (brain) | 1.6 | 1.3-2.1 | <0.001 |
| | HIF1A | 3091 | hypoxia-inducible factor 1 alpha | 1.4 | 1.1-1.7 | 0.007 |
| | CCT3 | 7203 | chaperonin containing TCP1, subunit 3 | 1.9 | 1.3-2.6 | <0.001 |
| mSD | HLA-DBPB1 | 3115 | MHC Class II, DPbeta 1 | 0.75 | 0.59-1.0 | 0.019 |
| | MAFK | 7375 | v-maf musculoaponeurotic fibrosarcoma oncogene homolog K (avian) | 1.1 | 0.82-1.5 | 0.45 |
| | RNF5 | 6048 | ring finger protein 5 | 1.2 | 0.92-1.6 | 0.18 |
| Risk Score | CCR7 | 1236 | chemokine (C-C motif) receptor 7 | 0.77 | 0.67-0.89 | <0.001 |
| | PAFAH1B3 | 5050 | platelet-activating factor acetylhydrolase, isoform 1b, gamma subunit 29kDa | 1.5 | 1.2-2.0 | 0.002 |

*HR denotes hazard ratios for death; CI denotes confidence interval. P values were determined by the log-rank test.

TABLE 3

Summary of hazard ratios for death (HR), 95% confidence intervals (CI) and p values for the training cohort (UHN) and all validation cohorts (Harvard, Michigan and Duke).

| Dataset | | mSD | | | Risk Score | | |
|---|---|---|---|---|---|---|---|
| | | HR | 95% CI | P* | HR | 95% CI | P* |
| UHN | All | 5.5 | 2.7-12 | <0.001 | 3.7 | 1.8-8.1 | <0.001 |
| | Stage I | 7.3 | 2.6-20 | <0.001 | 5.3 | 1.7-16 | <0.001 |
| Harvard | All | 2.2 | 0.77-6.3 | 0.03 | 1.6 | 0.95-2.6 | 0.01 |
| | Stage I | 2.6 | 0.5-14 | 0.09 | 2.2 | 1.1-4.5 | 0.007 |
| Michigan | All | 2.1 | 0.76-5.6 | 0.007 | 1.1 | 0.43-2.6 | 0.13 |
| | Stage I | 3.2 | 0.9-12 | 0.02 | 1.7 | 0.49-5.9 | 0.13 |
| Duke | All | 4.4 | 1.7-11 | <0.001 | 2.2 | 1.2-4.1 | 0.003 |
| | Stage I | 4.4 | 1.4-14 | 0.007 | 2.3 | 1.1-4.9 | 0.02 |

*P values determined by the log-rank test.

TABLE 4

C-Index scores and Risk Scores for individual genes ($\geq 0.65$). The RS was calculated by taking the integer value of the Cox proportional hazard model coefficient multiplied by a factor of 10 and truncated.

| Gene | C-Index | Coefficient | Score |
|---|---|---|---|
| STX1A | 0.689 | 0.431 | 4 |
| CCR7 | 0.670 | −0.314 | −3 |
| HIF1A | 0.661 | 0.348 | 3 |
| PAFAH1B3 | 0.659 | 0.135 | 1 |
| CCT3 | 0.653 | −0.007 | 0 |

TABLE 5

C-Index scores for clinical models alone (predictive ability of pathological stage and histology) compared to C-Index scores for a clinical and gene expression models combined for the mSD and RS gene classifiers (5a and 5b, respectively). The difference in C-Index scores and their 95% confidence intervals demonstrate that the 3-gene classifier significantly improves the predictive ability of a clinical model alone in the Toronto (training) and Duke patients.

| | Clinical Model | | Clinical + Gene Classifier Models | | Difference | |
|---|---|---|---|---|---|---|
| | C-Index | 95% CI | C-Index | 95% CI | Δ C-Index | 95% CI |
| a) C-Index values for mSD Classification | | | | | | |
| Toronto | 0.628 | 0.535-0.712 | 0.774 | 0.695-0.831 | 0.146 | 0.059-0.235 |
| Harvard | 0.678 | 0.594-0.748 | 0.701 | 0.614-0.773 | 0.022 | 0.000-0.091 |
| Michigan | 0.696 | 0.569-0.806 | 0.777 | 0.613-0.866 | 0.081 | −0.033-0.203 |
| Duke | 0.638 | 0.517-0.755 | 0.704 | 0.583-0.825 | 0.061 | −0.001-0.200 |
| b) C-Index values for Risk Score Classification | | | | | | |
| Toronto | 0.632 | 0.543-0.720 | 0.728 | 0.635-0.783 | 0.096 | 0.017-0.161 |
| Harvard | 0.639 | 0.575-0.696 | 0.680 | 0.602-0.731 | 0.041 | −0.018-0.079 |
| Michigan | 0.702 | 0.601-0.791 | 0.765 | 0.630-0.852 | 0.063 | −0.046-0.122 |
| Duke | 0.585 | 0.492-0.643 | 0.657 | 0.543-0.720 | 0.072 | 0.018-0.162 |

TABLE 6

Classification matrices indicating the correlation of the mSD and RS predictions by patient cohort.

| | | | Risk Score | | | |
|---|---|---|---|---|---|---|
| | | | Good | Poor | Not Classified* | P value** |
| UHN (n = 147) | mSD | Good | 65 | 23 | 4 | <0.001 |
| | | Poor | 5 | 44 | 6 | |
| | | Not Classified† | — | — | — | |
| Harvard (n = 125) | | Good | 49 | 26 | 0 | 0.007 |
| | | Poor | 1 | 7 | 0 | |
| | | Not Classified† | 16 | 26 | — | |
| Michigan (n = 86) | | Good | 33 | 12 | 0 | <0.001 |
| | | Poor | 0 | 16 | 0 | |
| | | Not Classified† | 6 | 19 | — | |
| Duke (n = 91) | | Good | 34 | 5 | 0 | <0.001 |
| | | Poor | 0 | 11 | 0 | |
| | | Not Classified† | 10 | 31 | — | |

*Cases not classified by the RS model as a result of missing expression data in these 10 patients.
†Cases not classified by mSD as a result of the imposed quality criterion.
**P-values determined by Fisher's exact test.

TABLE 7

Classifiers consistently identify a greater percentage of stage I patients who are at risk of death 3 years after surgery.

| | Patients | Probability of death at 3 years (%) | Good Prognosis | Probability of death at 3 years (%) | Poor Prognosis | Probability of death at 3 years (%) |
|---|---|---|---|---|---|---|
| mSD | | | | | | |
| UHN | 92 | 11 | 64 | 2 | 28 | 33 |
| Harvard | 49 | 19 | 46 | 18 | 3 | 33 |
| Michigan | 48 | 19 | 39 | 15 | 9 | 46 |
| Duke | 36 | 33 | 29 | 26 | 7 | 67 |
| C-Index | | | | | | |
| UHN | 86 | 11 | 48 | 0 | 38 | 24 |
| Harvard | 76 | 28 | 41 | 15 | 35 | 44 |

TABLE 7-continued

Classifiers consistently identify a greater percentage of stage
I patients who are at risk of death 3 years after surgery.

| | Patients | Probability of death at 3 years (%) | Good Prognosis | Probability of death at 3 years (%) | Poor Prognosis | Probability of death at 3 years (%) |
|---|---|---|---|---|---|---|
| Michigan | 67 | 19 | 33 | 7 | 34 | 30 |
| Duke | 67 | 38 | 36 | 24 | 31 | 53 |

LIST OF REFERENCES

1. Canadian Cancer Statistics 2005. Toronto, Canada: National Cancer Institute of Canada; 2005.
2. Mountain C F. Staging classification of lung cancer. A critical evaluation. Clin Chest Med 2002; 23(1):103-21.
3. Naruke T, Goya T, Tsuchiya R, Suemasu K. Prognosis and survival in resected lung carcinoma based on the new international staging system. J Thorac Cardiovasc Surg 1988; 96(3):440-7.
4. Wada H, Miyahara R, Tanaka F, Hitomi S. Postoperative adjuvant chemotherapy with PVM (Cisplatin+Vindesine+Mitomycin C) and UFT (Uracil+Tegaful) in resected stage I-II NSCLC (non-small cell lung cancer): a randomized clinical trial. West Japan Study Group for lung cancer surgery (WJSG). Eur J Cardiothorac Surg 1999; 15(4): 438-43.
5. Dunant A, Pignon J P, Le Chevalier T. Adjuvant chemotherapy for non-small cell lung cancer: contribution of the International Adjuvant Lung Trial. Clin Cancer Res 2005; 11(13 Pt 2):5017s-21s.
6. Winton T, Livingston R, Johnson D, et al. Vinorelbine plus cisplatin vs. observation in resected non-small-cell lung cancer. N Engl J Med 2005; 352(25):2589-97.
7. Strauss G M, Herndon J, Maddaus M A, et al. Randomized clinical trial of adjuvant chemotherapy with paclitaxel and carboplatin following resection in Stage IB non-small cell lung cancer (NSCLC): Report of Cancer and Leukemia Group B (CALGB) Protocol 9633. In: Journal of Clinical Oncology, 2004 ASCO Annual Meeting Proceedings (Post-Meeting Edition) Vol 22, No 14S (July 15 Supplement), 2004: 7019.
8. Rosell R, de Lena M, Carpagnano F, et al. ANITA: Phase III adjuvant vinorelbine (N) and cisplatin (P) versus observation in completely resected (stage I-III) non small cell lung cancer (NSCLC) patients (pts). Lung Cancer 2005; 49(Supplement 2):S3-S4.
9. Singhal S, Vachani A, Antin-Ozerkis D, Kaiser L R, Albelda S M. Prognostic implications of cell cycle, apoptosis, and angiogenesis biomarkers in non-small cell lung cancer: a review. Clin Cancer Res 2005; 11(11):3974-86.
10. Zhu C Q, Shih W, Ling C H, Tsao M S. Immunohistochemical markers of prognosis in non-small cell lung cancer: a review and proposal for a multiphase approach to marker evaluation. J Clin Pathol 2006; 59(8):790-800.
11. Bhattacharjee A, Richards W G, Staunton J, et al. Classification of human lung carcinomas by mRNA expression profiling reveals distinct adenocarcinoma subclasses. Proc Natl Acad Sci USA 2001; 98(24):13790-5.
12. Garber M E, Troyanskaya O G, Schluens K, et al. Diversity of gene expression in adenocarcinoma of the lung. Proc Natl Acad Sci USA 2001; 98(24):13784-9.
13. Beer D G, Kardia S L, Huang C C, et al. Gene-expression profiles predict survival of patients with lung adenocarcinoma. Nat Med 2002; 8(8):816-24.
14. Wigle D A, Jurisica I, Radulovich N, et al. Molecular profiling of non-small cell lung cancer and correlation with disease-free survival. Cancer Res 2002; 62(11):3005-8.
15. Ramaswamy S, Ross K N, Lander E S, Golub T R. A molecular signature of metastasis in primary solid tumors. Nat Genet 2003; 33(1):49-54.
16. Tomida S, Koshikawa K, Yatabe Y, et al. Gene expression-based, individualized outcome prediction for surgically treated lung cancer patients. Oncogene 2004; 23(31):5360-70.
17. Parmigiani G, Garrett-Mayer E S, Anbazhagan R, Gabrielson E. A cross-study comparison of gene expression studies for the molecular classification of lung cancer. Clin Cancer Res 2004; 10(9):2922-7.
18. Endoh H, Tomida S, Yatabe Y, et al. Prognostic model of pulmonary adenocarcinoma by expression profiling of eight genes as determined by quantitative real-time reverse transcriptase polymerase chain reaction. J Clin Oncol 2004; 22(5):811-9.
19. Jiang H, Deng Y, Chen H S, et al. Joint analysis of two microarray gene-expression data sets to select lung adenocarcinoma marker genes. BMC Bioinformatics 2004; 5:81.
20. Ein-Dor L, Zuk O, Domany E. Thousands of samples are needed to generate a robust gene list for predicting outcome in cancer. Proc Natl Acad Sci USA 2006; 103(15): 5923-8.
21. Bild A H, Yao G, Chang J T, et al. Oncogenic pathway signatures in human cancers as a guide to targeted therapies. Nature 2006; 439(7074):353-7.
22. Blackhall F H, Wigle D A, Jurisica I, et al. Validating the prognostic value of marker genes derived from a non-small cell lung cancer microarray study. Lung Cancer 2004; 46(2):197-204.
23. Tusher V G, Tibshirani R, Chu G. Significance analysis of microarrays applied to the ionizing radiation response. Proc Natl Acad Sci USA. 2001 Apr. 24; 98(9):5116-21.
24. Liu J, Blackhall F, Seiden-Long I, et al. Modeling of lung cancer by an orthotopically growing H460SM variant cell line reveals novel candidate genes for systemic metastasis. Oncogene 2004; 23(37):6316-24.
25. Barsyte-Lovejoy D, Lau S K, Boutros P C, et al. The c-Myc Oncogene Directly Induces the H19 Noncoding RNA by Allele-Specific Binding to Potentiate Tumorigenesis. Cancer Res 2006; 66(10):5330-7.
26. Yun J J, Heisler L E, Hwang, I I, et al. Genomic DNA functions as a universal external standard in quantitative real-time PCR. Nucleic Acids Res 2006; 34(12):e85.
27. Rubie C, Kempf K, Hans J, et al. Housekeeping gene variability in normal and cancerous colorectal, pancreatic, esophageal, gastric and hepatic tissues. Mol Cell Probes 2005; 19(2):101-9.
28. Morse P M, Feschbach H. Method of Steepest Descent. In: Methods of Theoretical Physics, Part I. New York: McGraw-Hill; 1953:pp. 434-43.

29. Harrell F E, Jr., Califf R M, Pryor D B, Lee K L, Rosati R A. Evaluating the yield of medical tests. JAMA: the Journal of the American Medical Association 1982; 247(18):2543-6.
30. Stephenson A J, Slawin K M. The value of radiotherapy in treating recurrent prostate cancer after radical prostatectomy. Nat Clin Pract Urol 2004; 1(2):90-6.
31. Ludwig J A, Weinstein J N. Biomarkers in cancer staging, prognosis and treatment selection. Nat Rev Cancer 2005; 5(11):845-56.
32. Petty R D, Nicolson M C, Kerr K M, Collie-Duguid E, Murray G I. Gene expression profiling in non-small cell lung cancer: from molecular mechanisms to clinical application. Clin Cancer Res 2004; 10(10):3237-48.
33. Lossos I S, Czerwinski D K, Alizadeh A A, et al. Prediction of survival in diffuse large-B-cell lymphoma based on the expression of six genes. N Engl J Med 2004; 350(18):1828-37.
34. Paik S, Shak S, Tang G, et al. A multigene assay to predict recurrence of tamoxifen-treated, node-negative breast cancer. N Engl J Med 2004; 351(27):2817-26.
35. Weigelt B, Peterse J L, van't Veer L J. Breast cancer metastasis: markers and models. Nat Rev Cancer 2005; 5(8):591-602.
36. Pugh C W, Ratcliffe P J. Regulation of angiogenesis by hypoxia: role of the HIF system. Nat Med 2003; 9(6):677-84.
37. Grabowski P, Schonfelder J, Ahnert-Hilger G, et al. Expression of neuroendocrine markers: a signature of human undifferentiated carcinoma of the colon and rectum. Virchows Arch 2002; 441(3):256-63.
38. Graff L, Castrop F, Bauer M, Hofler H, Gratzl M. Expression of vesicular monoamine transporters, synaptosomal-associated protein 25 and syntaxin1: a signature of human small cell lung carcinoma. Cancer Res 2001; 61(5):2138-44.
39. Bascom J L, Fata J E, Hirai Y, Sternlicht M D, Bissell M J. Epimorphin overexpression in the mouse mammary gland promotes alveolar hyperplasia and mammary adenocarcinoma. Cancer Res 2005; 65(19):8617-21.
40. Potti A, Mukherjee S, Petersen R, et al. A genomic strategy to refine prognosis in early-stage non-small-cell lung cancer. N Engl J Med 2006; 355(6):570-80.
41. Raponi M, Zhang Y, Yu J, et al. Gene expression signatures for predicting prognosis of squamous cell and adenocarcinomas of the lung. Cancer Res 2006; 66(15):7466-72.
42. van't Veer L J, Dai H, van de Vijver M J, et al. Gene expression profiling predicts clinical outcome of breast cancer. Nature 2002; 415(6871):530-6.
43. van de Vijver M J, He Y D, van't Veer L J, et al. A gene-expression signature as a predictor of survival in breast cancer. N Engl J Med 2002; 347(25):1999-2009.
44. Zeeberg B R, Feng W, Wang G, Wang M D, Fojo A T, Sunshine M, Narasimhan S, Kane D W, Reinhold W C, Lababidi S, Bussey K J, Riss J, Barrett J C, Weinstein J N. GoMiner: a resource for biological interpretation of genomic and proteomic data. Genome Biol. 2003; 4(4):R28.

The invention claimed is:
1. A method of prognosing a subject with early stage non-small cell lung cancer (NSCLC), comprising the steps of:
(a) determining the expression levels of STX1A, HIF1A, CCT3, MAFK, RNF5 and HLA-DPB1 in a lung tumor test sample from the subject; and
(b) comparing the expression levels so determined with expression levels of STX1A, HIF1A, CCT3, MAFK, RNF5 and HLA-DPB1 in a lung tumor control from an early stage NSCLC subject or group of early stage NSCLC subjects,
wherein higher levels of STX1A, HIF1A, CCT3, MAFK, and RNF5 and lower levels of HLA-DPB1 in the subject as compared to the control indicates a poor prognosis; or
(c) determining the expression levels of STX1A, CCR7, and HIF1A in a lung tumor test sample from the subject; and
(d) comparing the expression levels so determined with expression levels of STX1A, CCR7, and HIF1A in a control from an early stage NSCLC subject or group of early stage NSCLC subjects,
wherein higher levels of STX1A and HIF1A and lower levels of CCR7 in the subject as compared to the control indicates a poor prognosis.
2. The method according to claim 1, comprising the steps of:
(a) determining the expression levels of STX1A, HIF1A, CCT3, MAFK, RNF5 and HLA-DPB1 in a lung tumor test sample from the subject; and
(b) comparing the expression levels so determined with expression levels of STX1A, HIF1A, CCT3, MAFK, RNF5 and HLA-DPB1 in a lung tumor control from an early stage NSCLC subject or group of early stage NSCLC subjects,
wherein higher levels of STX1A, HIF1A, CCT3, MAFK, and RNF5 and lower levels of HLA-DPB1 in the subject as compared to the control indicates a poor prognosis.
3. The method according to claim 2, wherein the subject has stage I NSCLC.
4. The method according to claim 2, wherein the subject has stage II NSCLC.
5. The method of claim 1, comprising the steps of:
(a) determining the expression levels of STX1A, CCR7, and HIF1A in a lung tumor test sample from the subject; and
(b) comparing the expression levels so determined with expression levels of STX1A, CCR7, and HIF1A in a lung tumor control from an early stage NSCLC subject or group of early stage NSCLC subjects,
wherein higher levels of STX1A and HIF1A and lower levels of CCR7 in the subject as compared to the control indicates a poor prognosis.
6. The method according to claim 5, wherein the subject has stage I NSCLC.
7. The method according to claim 5, wherein the subject has stage II NSCLC.
8. The method according to claim 1, wherein the control is a specific value obtained from an early stage NSCLC subject or group of early stage NSCLC subjects.
9. The method according to claim 2, wherein the control is a specific value obtained from an early stage NSCLC subject or group of early stage NSCLC subjects.
10. The method according to claim 5, wherein the control is a specific value obtained from an early stage NSCLC subject or group of early stage NSCLC subjects.
11. The method according to claim 1, wherein the control is a sample obtained from an early stage NSCLC subject or group of early stage NSCLC subjects.
12. The method according to claim 2, wherein the control is a sample obtained from an early stage NSCLC subject or group of early stage NSCLC subjects.
13. The method according to claim 5, wherein the control is a sample obtained from an early stage NSCLC subject or group of early stage NSCLC subjects.

* * * * *